US008649858B2

(12) United States Patent
Griffith et al.

(10) Patent No.: US 8,649,858 B2
(45) Date of Patent: Feb. 11, 2014

(54) ARCHITECTURES FOR AN IMPLANTABLE MEDICAL DEVICE SYSTEM

(75) Inventors: Paul J. Griffith, Moorpark, CA (US);
Jordi Parramon, Valencia, CA (US);
Goran N. Marnfeldt, Hollviken (SE);
Daniel Aghassian, Los Angeles, CA (US); Kiran Nimmagadda, Valencia, CA (US); Emanuel Feldman, Simi Valley, CA (US); Jess W. Shi, Winnetka, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 615 days.

(21) Appl. No.: 11/767,636

(22) Filed: Jun. 25, 2007

(65) Prior Publication Data

US 2008/0319497 A1    Dec. 25, 2008

(51) Int. Cl.
*A61N 1/36*    (2006.01)
*A61N 1/08*    (2006.01)

(52) U.S. Cl.
USPC ........... 607/4; 607/28; 607/66; 607/9; 607/59

(58) Field of Classification Search
USPC ............................................................ 607/4
See application file for complete search history.

(56) References Cited

U.S. PATENT DOCUMENTS

| | | | |
|---|---|---|---|
| 4,562,841 A | | 1/1986 | Brockway et al. |
| 5,188,106 A | * | 2/1993 | Nappholz et al. ............... 607/24 |
| 5,215,083 A | * | 6/1993 | Drane et al. ....................... 607/4 |
| 5,464,435 A | | 11/1995 | Neumann |
| 5,603,726 A | | 2/1997 | Schulman et al. |
| 5,735,887 A | * | 4/1998 | Barreras et al. ................. 607/60 |
| 5,876,425 A | | 3/1999 | Gord et al. |
| 5,941,906 A | * | 8/1999 | Barreras et al. ................. 607/66 |

(Continued)

FOREIGN PATENT DOCUMENTS

| | | |
|---|---|---|
| EP | 1785884 | 5/2007 |
| JP | 06-154344 | 6/1994 |

(Continued)

OTHER PUBLICATIONS

International Search Report dated Jul. 24, 2008 regarding application No. PCT/US2008/059134.

(Continued)

*Primary Examiner* — Carl H Layno
*Assistant Examiner* — Jon Eric C Morales
(74) *Attorney, Agent, or Firm* — Wong, Cabello, Lutsch, Rutherford & Brucculeri, LLP.

(57) ABSTRACT

An improved architecture for an implantable medical device such as an implantable pulse generator (IPG) is disclosed. In one embodiment, the various functional blocks for the IPG are incorporated into a signal integrated circuit (IC). Each of the functional blocks communicate with each other, and with other off-chip devices if necessary, via a centralized bus governed by a communication protocol. To communicate with the bus and to adhere to the protocol, each circuit block includes bus interface circuitry adherent with that protocol. Because each block complies with the protocol, any given block can easily be modified or upgraded without affecting the design of the other blocks, facilitating debugging and upgrading of the IPG circuitry. Moreover, because the centralized bus can be taken off the integrated circuit, extra circuitry can easily be added off chip to modify or add functionality to the IPG without the need for a major redesign of the main IPG IC.

27 Claims, 10 Drawing Sheets

(56) References Cited

U.S. PATENT DOCUMENTS

| | | |
|---|---|---|
| 6,317,633 B1 * | 11/2001 | Jorgenson et al. ............ 607/28 |
| 6,516,227 B1 | 2/2003 | Meadows et al. |
| 6,731,985 B2 * | 5/2004 | Poore et al. .................... 607/28 |
| 6,738,670 B1 * | 5/2004 | Almendinger et al. ......... 607/60 |
| 6,754,533 B1 | 6/2004 | Helfinstine et al. |
| 2002/0052633 A1 | 5/2002 | Prutchi et al. |
| 2003/0055406 A1 | 3/2003 | Lebel et al. |
| 2003/0083708 A1 * | 5/2003 | Bradley et al. ................. 607/27 |
| 2004/0049246 A1 * | 3/2004 | Almendinger et al. ......... 607/60 |
| 2004/0059396 A1 | 3/2004 | Reinke et al. |
| 2004/0088015 A1 * | 5/2004 | Casavant et al. ............... 607/14 |
| 2006/0058588 A1 | 3/2006 | Zdeblick |
| 2007/0027485 A1 | 2/2007 | Kallmyer et al. |
| 2007/0078498 A1 | 4/2007 | Rezai et al. |
| 2007/0135868 A1 | 6/2007 | Shi et al. |

FOREIGN PATENT DOCUMENTS

| | | |
|---|---|---|
| JP | 08-038626 | 2/1996 |
| WO | 0154753 A2 | 8/2001 |
| WO | 2005/061044 | 7/2005 |
| WO | 2006/029090 | 3/2006 |
| WO | 2006/118846 | 11/2006 |
| WO | 2007/027570 | 3/2007 |

OTHER PUBLICATIONS

International Search Report dated Nov. 7, 2008 regarding application No. PCT/US2008/059134.

Correspondence from Japanese Patent Office for related Japanese Patent Application No. 2010-514892, Dec. 27, 2011, (with English Translation).

* cited by examiner

ARCHITECTURES FOR AN IMPLANTABLE MEDICAL DEVICE SYSTEM

FIELD OF THE INVENTION

The present invention relates generally to implantable medical devices, and more particularly, to improved architectures for the circuitry in an implantable medical device.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The present invention may find applicability in all such applications, although the description that follows will generally focus on the use of the invention within a Spinal Cord Stimulation (SCS) system, such as that disclosed in U.S. Pat. No. 6,516,227 ("the '227 patent"), which is incorporated herein by reference in its entirety.

Figures 1A, 1B:
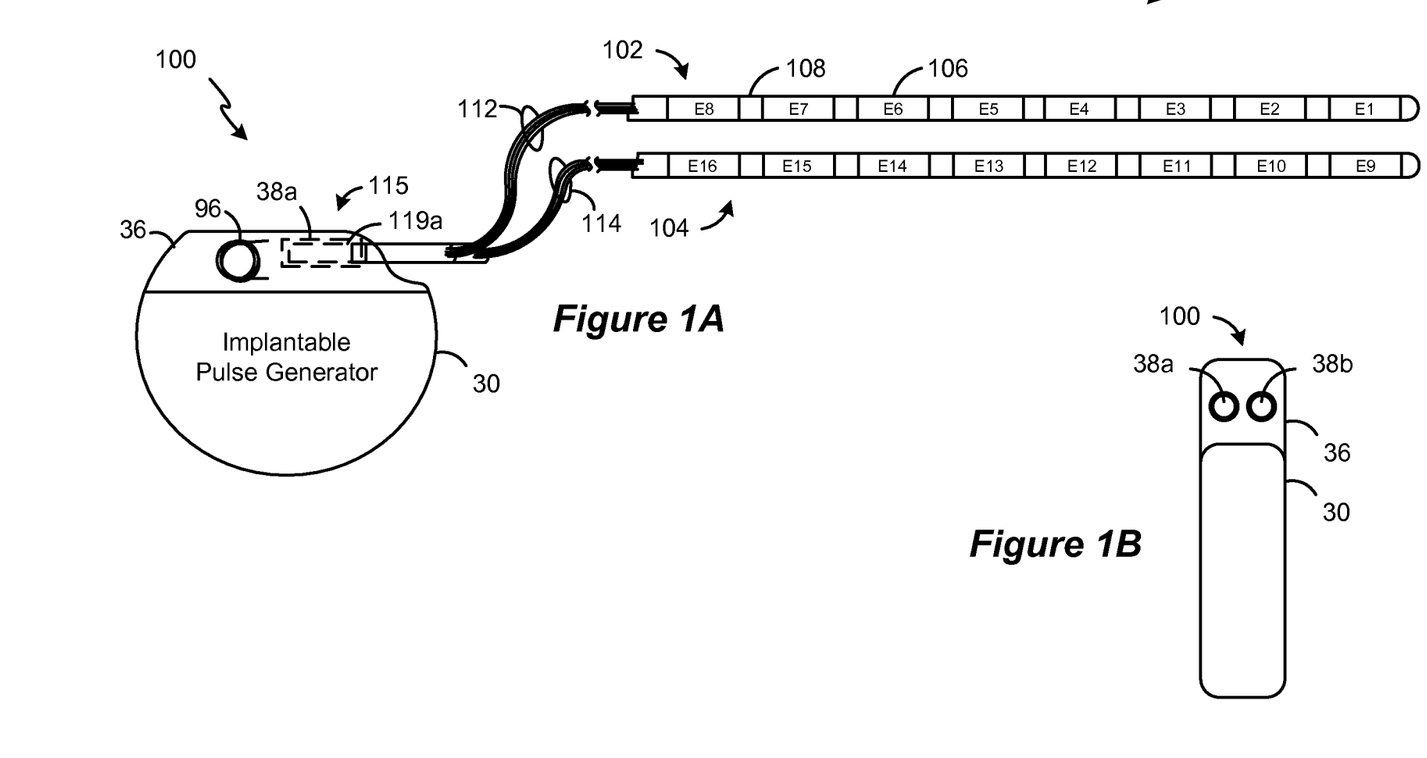
FIGS. 1A and 1B show an implantable pulse generator (IPG), and the manner in which an electrode array is coupled to the IPG in accordance with the prior art.

Spinal cord stimulation is a well-accepted clinical method for reducing pain in certain populations of patients. As shown in FIGS. 1A and 1B, a SCS system typically includes an Implantable Pulse Generator (IPG) 100, which includes a biocompatible case 30 formed of titanium for example. The case 30 usually holds the circuitry and power source or battery necessary for the IPG to function. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112, 114, coupled to each electrode. The signal wires 112 and 114 are connected to the IPG 100 by way of an interface 115, which may be any suitable device that allows the leads 102 and 104 (or a lead extension, not shown) to be removably connected to the IPG 100. Interface 115 may comprise, for example, an electromechanical connector arrangement including lead connectors 38a and 38b configured to mate with corresponding connectors 119a and 119b on the leads 102 and 104. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary. The electrode array 110 is typically implanted along the dura of the spinal cord, and the IPG 100 generates electrical pulses that are delivered through the electrodes 106 to the nerve fibers within the spinal column. The IPG 100 itself is then typically implanted somewhat distantly in the buttocks of the patient.

Figure 2:
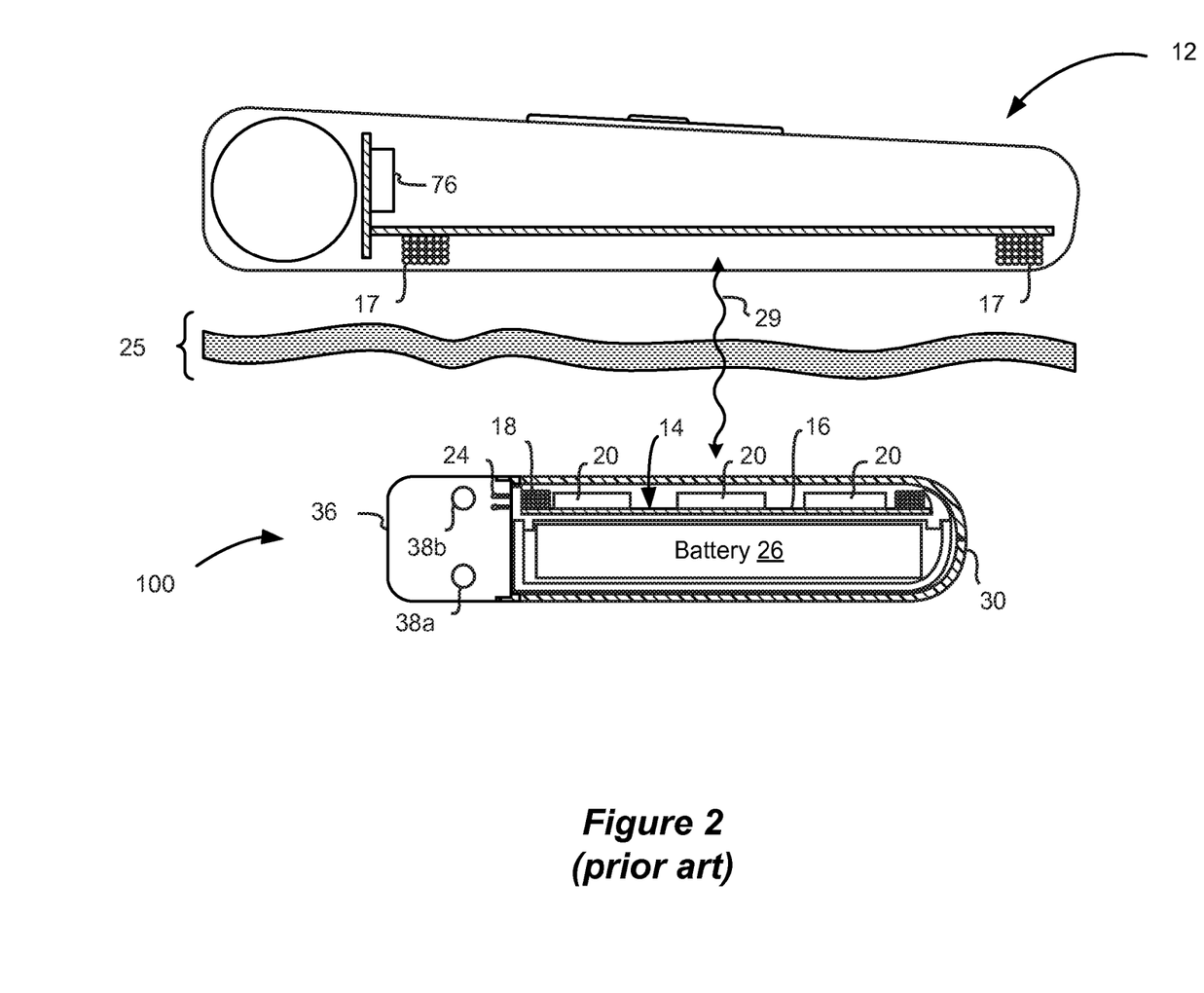
FIG. 2 shows the IPG in relation to an external charger in accordance with the prior art.

As shown in FIG. 2, an IPG 100 typically includes an electronic substrate assembly 14 including a printed circuit board (PCB) 16, along with various electronic components 20, such as microprocessors, integrated circuits, and capacitors, mounted to the PCB 16. Ultimately, the electronic circuitry performs a therapeutic function, such as neurostimulation. A feedthrough assembly 24 routes the various electrode signals from the electronic substrate assembly 14 to the lead connectors 38a, 38b, which are in turn coupled to the leads 102 and 104 (see FIGS. 1A and 1B). The IPG 100 further comprises a header connector 36, which among other things houses the lead connectors 38a, 38b. The IPG 100 can further include a telemetry antenna or coil 96 (FIG. 1A) mounted within the header connector 36 for transmission and receipt of data to and from an external device such as a hand-held or clinician programmer (not shown). As noted earlier, the IPG 100 usually also includes a power source 26, usually a rechargeable battery 26. The power source 26 can be recharged transcutaneously by an external charger 12. Specifically, when active during a charging session, the external charger 12 energizes its charging coil 17, which in turn induces a current in the charging coil 18 in the IPG 100. This induced current is rectified and ultimately used to charge the power source 26 through the patient's flesh 25.

Further details concerning the structure and function of typical IPGs and IPG systems are disclosed in U.S. patent application Ser. No. 11/305,898, filed Dec. 14, 2005, which is incorporated herein by reference.

Figure 3:
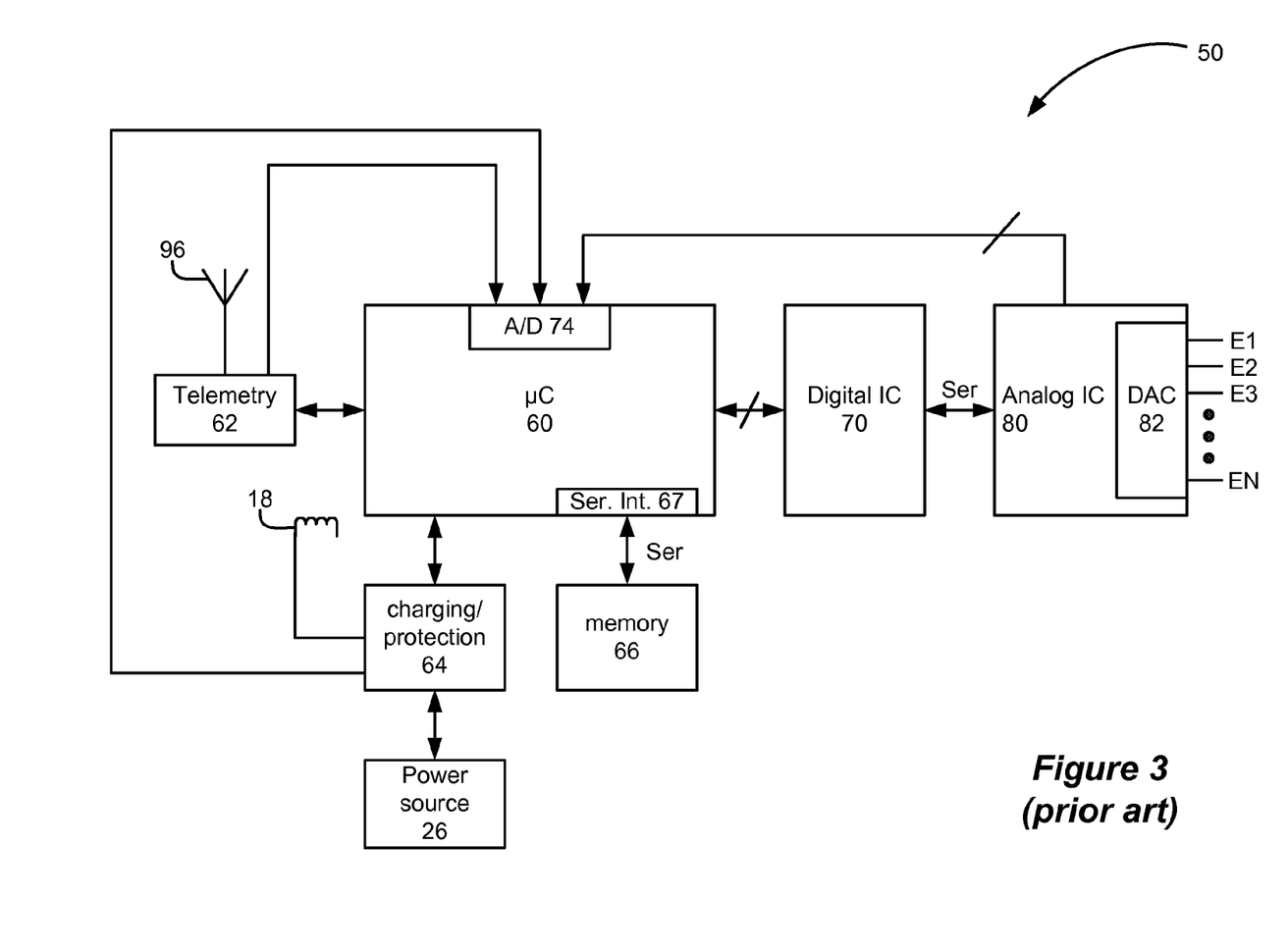
FIG. 3 shows the architecture of the circuitry within the IPG in accordance with the prior art.

A traditional architecture 50 for the circuitry inside of an IPG 100 is shown in FIG. 3. As one skilled in the art will appreciate, FIG. 3 depicts the IPG 100's circuitry at a relatively high level sufficient to understand the points this disclosure makes. The architecture 50 contains basic circuit blocks for executing various electrical functions in the IPG 100. For example, telemetry circuit 62 is coupled to coil 96, and operates to send and receive data to and from an external controller (not shown). Charging and battery protection circuitry 64 is similarly coupled to charging coil 18, and intervenes between the power source 26 and the rest of the circuitry. Both of these circuits 62 and 64 are coupled to a microcontroller 60, which as can be noticed is central to the design of the architecture 50. Programs and data needed by the microcontroller 60 upon power up are stored in a memory 66, preferably a serial nonvolatile memory, which is coupled to the microcontroller 60 by a serial interface 67.

Circuitry involved in providing a predictable therapy of stimulation is provided by a digital integrated circuit (IC) 70 and an analog IC 80. In one application, the digital IC 70 contains stimulation control logic, such as the various timers that are used by the IPG's timing channels to provide a stimulation pulse train with a particular timing. The analog IC 80 receives data from the digital IC 70 via a serial link, where such data is converted to analog signals by a digital-to-analog converter (DAC) 82, which in turn ultimately provides the stimulus to the electrodes (E1 . . . EN). Additionally, an analog-to-digital (A/D) converter 74 is used to inform the microcontroller 60 of various analog voltages being produced or monitored on the analog IC 80, such as various reference voltages, the stimulation compliance voltage, etc., and within the charging 64 and telemetry 62 blocks. Although shown as integrated with the microcontroller 60, the A/D converter 74 could also be a discrete component outside of the microcontroller 60.

In one embodiment, the microcontroller 60, the digital IC 70, and the analog IC 80 comprise discrete ICs each comprising one of the components 20 on the IPG's printed circuit board 16 (see FIG. 1). Other functional blocks in the architecture 50 might comprise other components 20, which might not be integrated but rather formed at least in part of discrete components.

Having briefly described the functional blocks in architecture 50, it should be noted that it is not important to the present disclosure to understand the detailed workings of those blocks. (The reader can consult the above-incorporated '898 application should a greater knowledge of each of the functional blocks be desired). Instead, what is important to understand is the manner in which the functional blocks are interconnected. As one skilled in the art will understand, central to the operation of architecture 50 is the microcontroller 60, which ultimately receives and issues all commands from and to the other blocks. Furthermore, it can be noticed that the various interconnections between the blocks vary in type and complexity, with some connections being serial in nature, and others comprising single data lines or comprising data digital busses. Moreover, some of the blocks lack direct connections with other blocks, and hence must communicate through intermediary blocks. For example, the microcontroller 60 must, at least in part, communicate with the analog IC 80 through the digital IC 70.

Such inter-connectivity adds to the expense of the IPG 100 and its complexity. Moreover, it also makes it difficult to adapt a particular architecture to desired changes and/or newer IPG revisions. For example, the changing of one of the functional blocks may require significant corresponding changes in other functional blocks, making upgrades or revisions expensive.

Additionally, space within an IPG 100 is limited, because IPGs are preferably as small as possible to make the implant as unobtrusive as possible for the patient. In this regard, the architecture 50 of FIG. 3 is further problematic because of its requirement of separate IC used for the microcontroller 60, the digital IC 70, and the analog IC 80 (and possibly other components). Having numerous components generally negatively impacts the reliability of the circuit, and increases power consumption, generally a big concern for a power-limited IPG.

This disclosure presents a solution to this problem in the art of implantable medical devices via an improved IPG architecture.

DETAILED DESCRIPTION

An improved architecture for an implantable medical device such as an implantable pulse generator (IPG) is disclosed. In one embodiment, the various functional blocks for the IPG are incorporated into a single integrated circuit (IC). Each of the functional blocks communicate with each other, and with other off-chip devices if necessary, via a centralized bus governed by a communication protocol. To communicate with the bus and to adhere to the protocol, each circuit block includes bus interface circuitry adherent with that protocol. Because each block complies with the protocol, any given block can easily be modified or upgraded without affecting the design of the other blocks, facilitating debugging and upgrading of the IPG circuitry. Moreover, because the centralized bus can be taken off the integrated circuit, extra circuitry can easily be added off chip to modify or add functionality to the IPG without the need for a major redesign of the main IPG IC.

Figure 4:
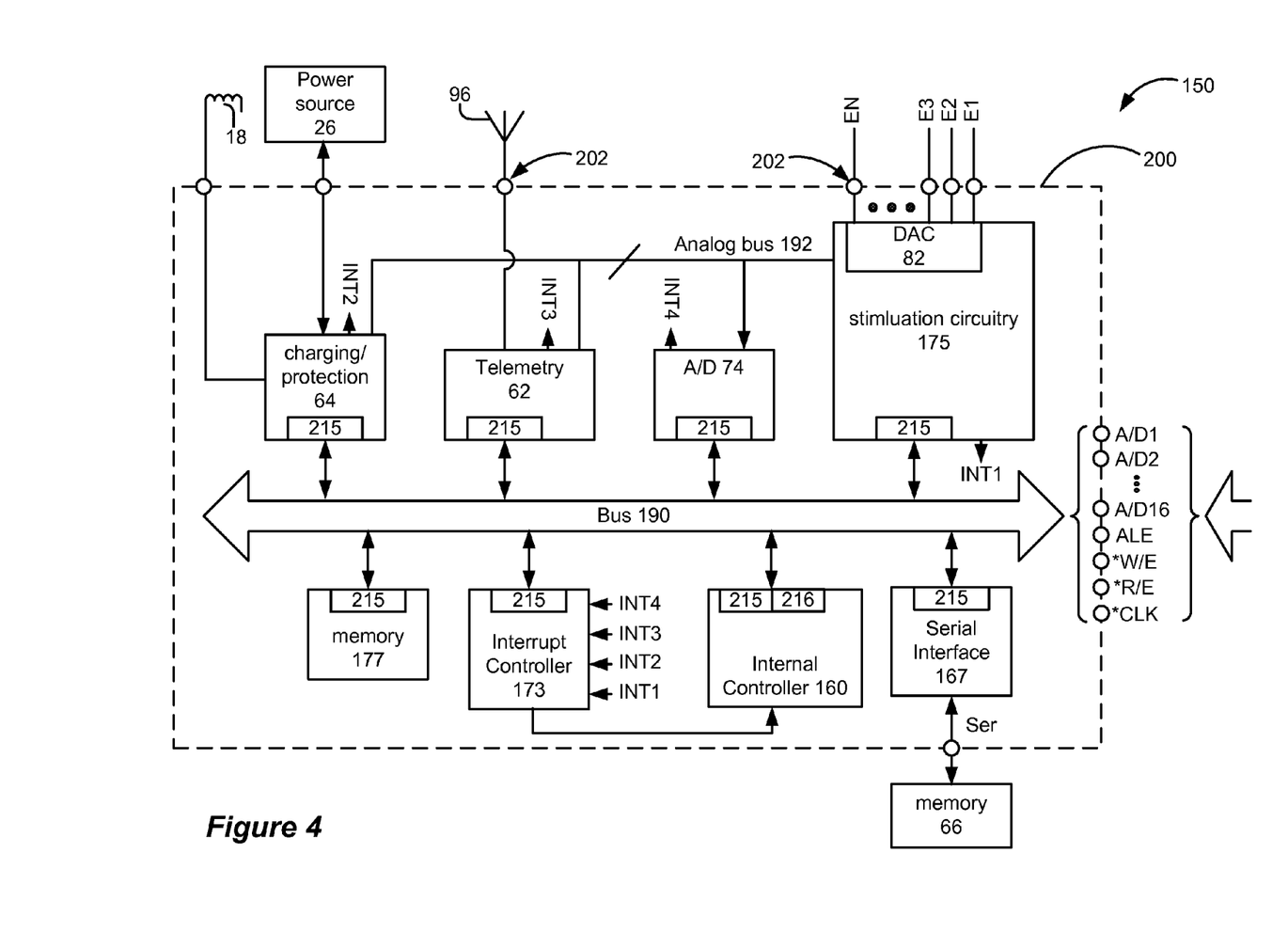
FIG. 4 shows an improved architecture for an IPG incorporating a centralized bus operating with the various functional blocks in accordance with a communication protocol.

FIG. 4 shows one example of the improved IPG architecture 150. As a comparison to FIG. 3 shows, most of the functional blocks in FIG. 4 correspond to circuit blocks of FIG. 3, and thus perform similar functions in the new architecture 150. However, in a major difference, all of the functional blocks in the improved architecture 150 are coupled to a centralized bus 190. In the embodiment illustrated in this disclosure, the centralized bus 190 is a parallel bus containing a plurality of multiplexed address and data lines operating in parallel. However, this is not strictly necessary, and instead bus 190 can comprise a serial bus as well.

In a preferred embodiment, each of the illustrated functional blocks are integrated within a single integrated circuit (IC) 200. Because the IPG IC 200 as illustrated contains both analog and digital signals, the IC 200 would comprise a mixed mode chip. However, it is not strictly necessary that the architecture 150 be realized on a single IC 200 as shown. Moreover, it should be understood that certain other circuitry components within the IPG 100 (such as the data and charging coils 96 and 18, the power source 26, and external memory 66, etc.) would logically reside outside of the IC 200. That being said, it is still preferred that as many as possible of the functional blocks within the IPG be consolidated on the IC 200, as this increases yield, increases reliability, decreases space of the electronic circuitry within the IPG, decreases power consumption of the circuitry within the IPG 100, etc.

Each of the various functional blocks in the improved IPG architecture 150 communicate with the centralized bus 190 via bus interface circuitry 215, which will be discussed in further detail later. Preferably, all other non-bus-based communications between the functional blocks are kept to a minimum, but some such communications are beneficial. For example, as shown, various interrupts (INT1, INT2, . . . ) communicate directly with an interrupt controller 173, which allows their issuance to be immediately recognized without the potential delays involved in protocol-based communication through the centralized bus 190. For example, INT2 can inform the interrupt controller 173 if the power source 26 is charged to a dangerous level, so that operation of the IC 200 might be temporarily curtailed if necessary. In another off-bus communication, an analog bus 192 is used to send various analog signals to a A/D block 74 where such voltages can be digitized and made available to other functional blocks via the centralized bus 190 as needed.

While it is not terribly important to the disclosed improved IPG architecture 150 to understand the operation of each of the functional blocks, note from FIG. 4 that the digital IC 70 and the analog IC 80 of the prior art (FIG. 3) have effectively been consolidated into a mixed-mode stimulation circuitry block 175, which both sets the timing, magnitude, and polarity of the stimulation pulses appearing at each of the electrodes, Ex.

In another important difference with the architecture 50 of the prior art (FIG. 3), notice that the centralized microcontroller 60 (FIG. 3) has been replaced by an internal controller 160. Given the paralleled nature of the centralized bus 190, control within the IC 200 is less focused on one source, and instead control is essentially divided between the controller 160 and the various functional blocks, with the controller 160 acting as the "master." Specifically, each functional block contains set up and status registers (not shown). The controller 160, upon initialization, writes to the set up registers to configure and enable each functional block. The status registers are then set by each functional block and read by the controller 160 to query for status and other results. Aside from such control imposed by the master controller 160, many of the functional blocks outside of the controller 160 can employ simple state machines to manage their operation, which state machines are enabled and modified via the set up registers. Because it acts as the master, the bus interface circuitry 215 of the internal controller 160 is somewhat unique and, for example, contains driver circuitry 216 for the control signals used by the communications protocol (e.g., ALE, W/E, and R/E) which would be lacking in the bus interface circuitry 215 of other functional blocks within the IC 200.

As can be seen in FIG. 4, the IC 200 contains several external terminals 202 (e.g., pins, solder bumps, etc.), such as those necessary to connect the power source 26, to connect the coils 18, 96, to connect the external memory 66, and to connect the stimulation electrodes. In a preferred embodiment, other external terminals 202 are dedicated to the various signals that comprise the centralized bus 190 to allow this bus to communicate with other devices outside of the IC 200, as will be explained in more detail later.

Figure 5:
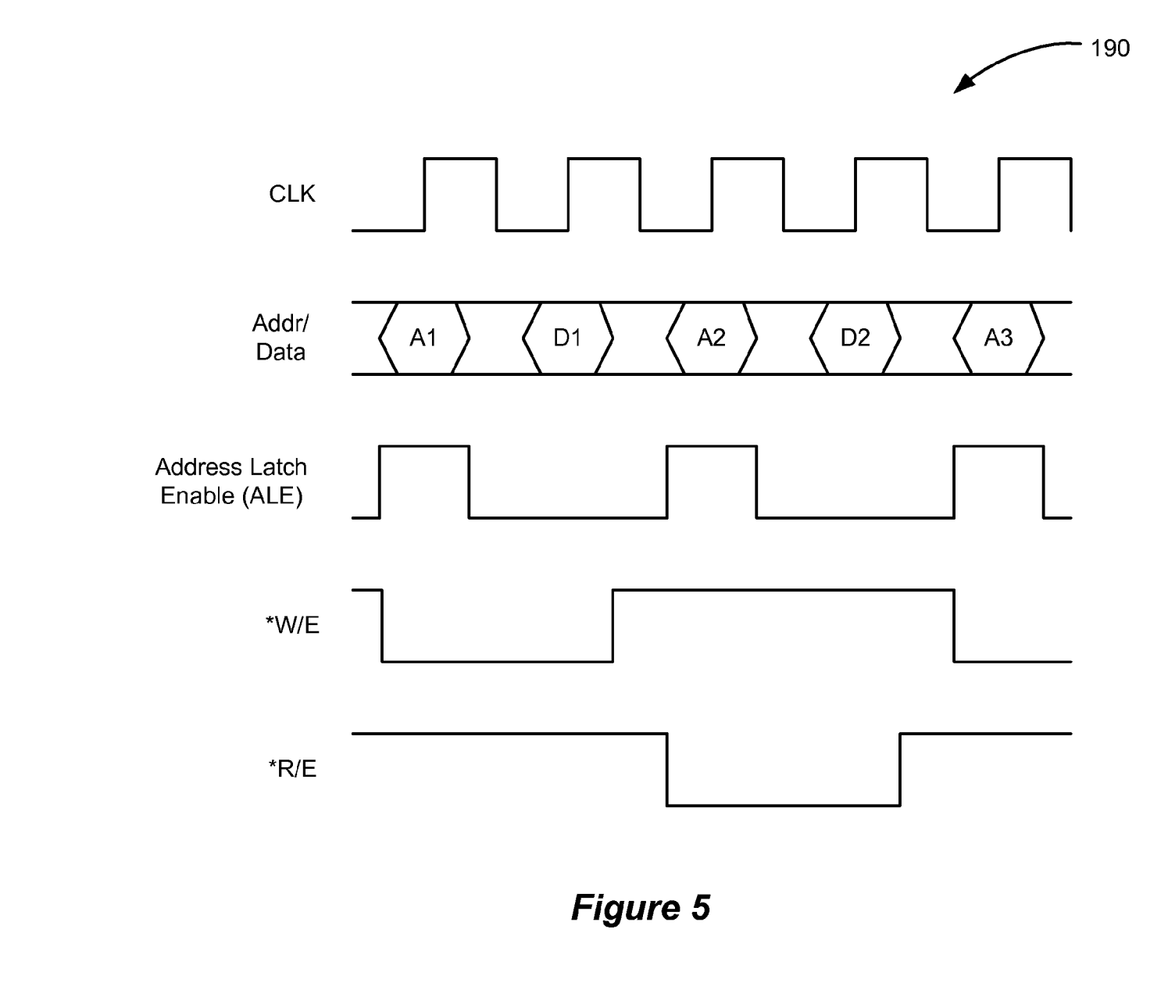
FIG. 5 shows the various signal on the centralized bus of FIG. 4 and indicates the communication protocol used on the bus.

The various signals comprising the bus 190 can be seen in FIG. 5, which also discloses one possible protocol for communications on the bus. As shown, the centralized bus 190 comprises a clock signal (CLK) for synchronization, time-multiplexed address and data signals (A/Dx); an address latch enable signal (ALE); an active-low write enable signal (*W/E), and an active-low read enable signal (*R/E). The centralized bus 90 may comprise sixteen address/data signals, but of course this number can change depending on system requirements.

As one skilled in the art will appreciate, communications in an IPG system such as one including the IC 200 of FIG. 4 can operate relatively slowly compared to other computerized systems. This eases the requirements of the protocol used on the centralized bus 190, and allows for a relatively simple and comparatively-slow protocol to be used. For example, the frequency for the clock signal, CLK, can be in the range of 32 kHZ to 1 MHz. Such a frequency is generally slow for a computerized protocol, but is suitably fast compared to operation of the IPG, which typically provide stimulation pulses on the order of tens of microseconds to milliseconds.

As shown, the protocol uses a fairly simple address-before-data scheme in which an address is followed by pertinent data for that address, etc. To help discern between address and data, the address latch enable signal (ALE) is active only upon the issuance of an address, which allows the address to be latched upon the rising edge of the clock. Whether the data corresponding to a particular address is to be written or read depends on the assertion of the write and read enable signals (*W/E; *R/E). Of course, this protocol is merely exemplary and other protocols and formats could be use for communication on the centralized bus 190.

The nature of the protocol of FIG. 5 means that all functional blocks coupled to the centralized bus 190 must be designated an address, or more likely, a range of addresses. For example, the address for a data register holding the value for the compliance voltage (in A/D block 74) might be ADDR [3401] while the address for a bandgap reference voltage might be ADDR[3402]; the address for the magnitude of stimulation to be provided by electrode E6 (in stimulation circuitry block 175) may be ADDR[7655], while the duration of that pulse may be stored at ADDR[7656], etc.

Figure 6:
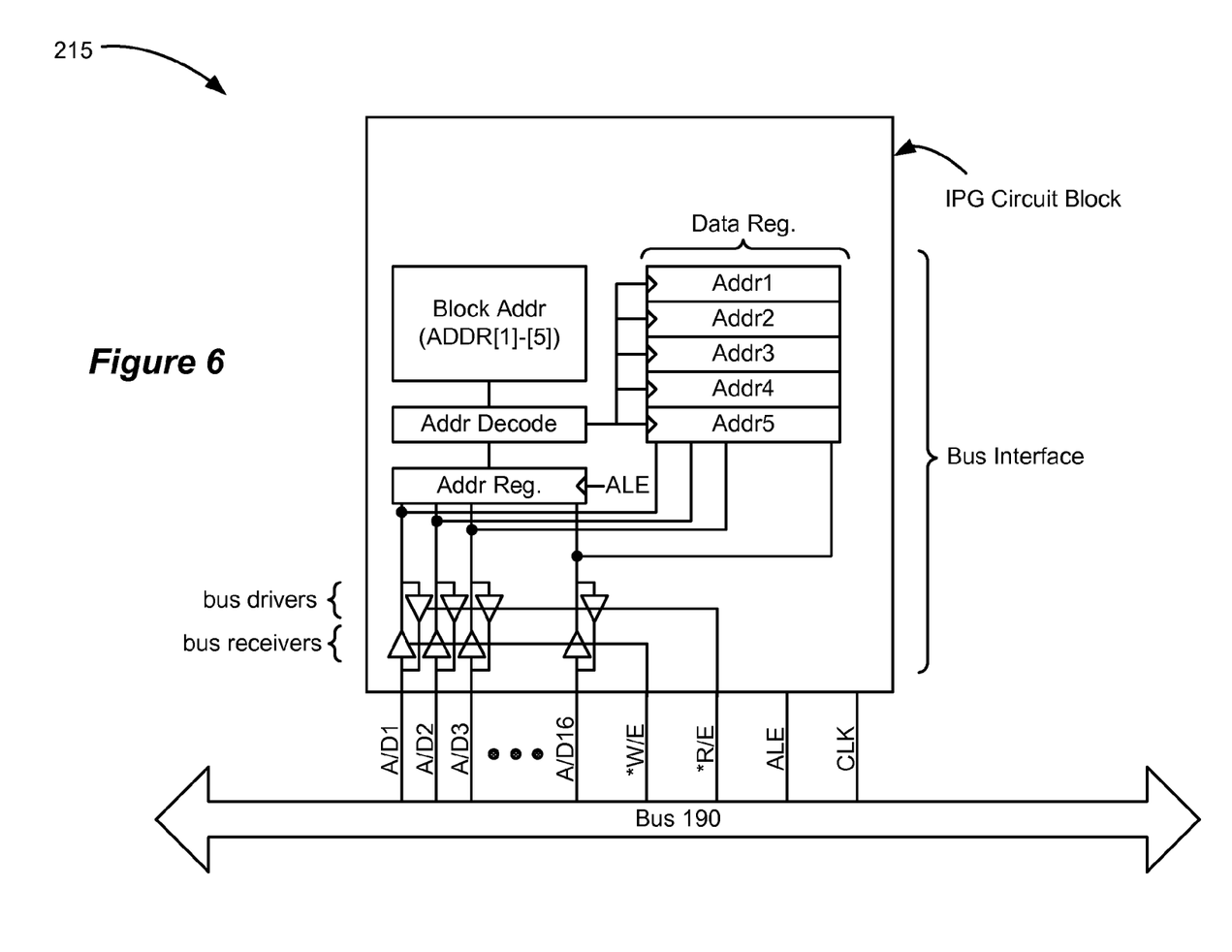
FIG. 6 shows the basic structure of the bus interface circuitry used by each functional block communicating with the centralized bus of FIG. 4.

To assist the various functional blocks in recognizing pertinent addresses, and to ensure each block's ability to function in accordance with the centralized bus 190's protocol, each block contains bus interface circuitry 215, which is shown in FIG. 6. One skilled in the art will well understand the operation of bus interface circuitry 215, and so it is explained at a general level. As noted earlier, one or more addresses may be associated with each functional block, such as ADDR[1]-[5] in the simple example of FIG. 6. When such addresses are received at the various blocks, each block decodes those addresses to determine a match, i.e., to determine if the address corresponds to one of the addresses pointing to that block. If so, and depending of whether data is to be written to of read from the address in question, bus drivers (in the case of a read) or bus receivers (in the case of a write) are enabled, and the data is then written to or read from the block's data register. To adhere to this protocol, the actual functional circuitry in the block (not shown in FIG. 6) must interface with the data register appropriately as one skilled in the art understands.

With the bus interface circuitry 215 allowing each functional block to communicate using the protocol established for the bus 190, it now becomes a relatively simple endeavor to make changes to the various functional blocks to fix circuit errors, and/or to upgrade the IC 200 for use in next-generation IPGs. This is because each of the blocks' circuitry can be changed without worries that such changes will necessitate other changes in related blocks, or otherwise perturb the operation of other blocks. Functional blocks can be independently designed and verified in parallel, saving time and hassle during the design process.

Figure 7:
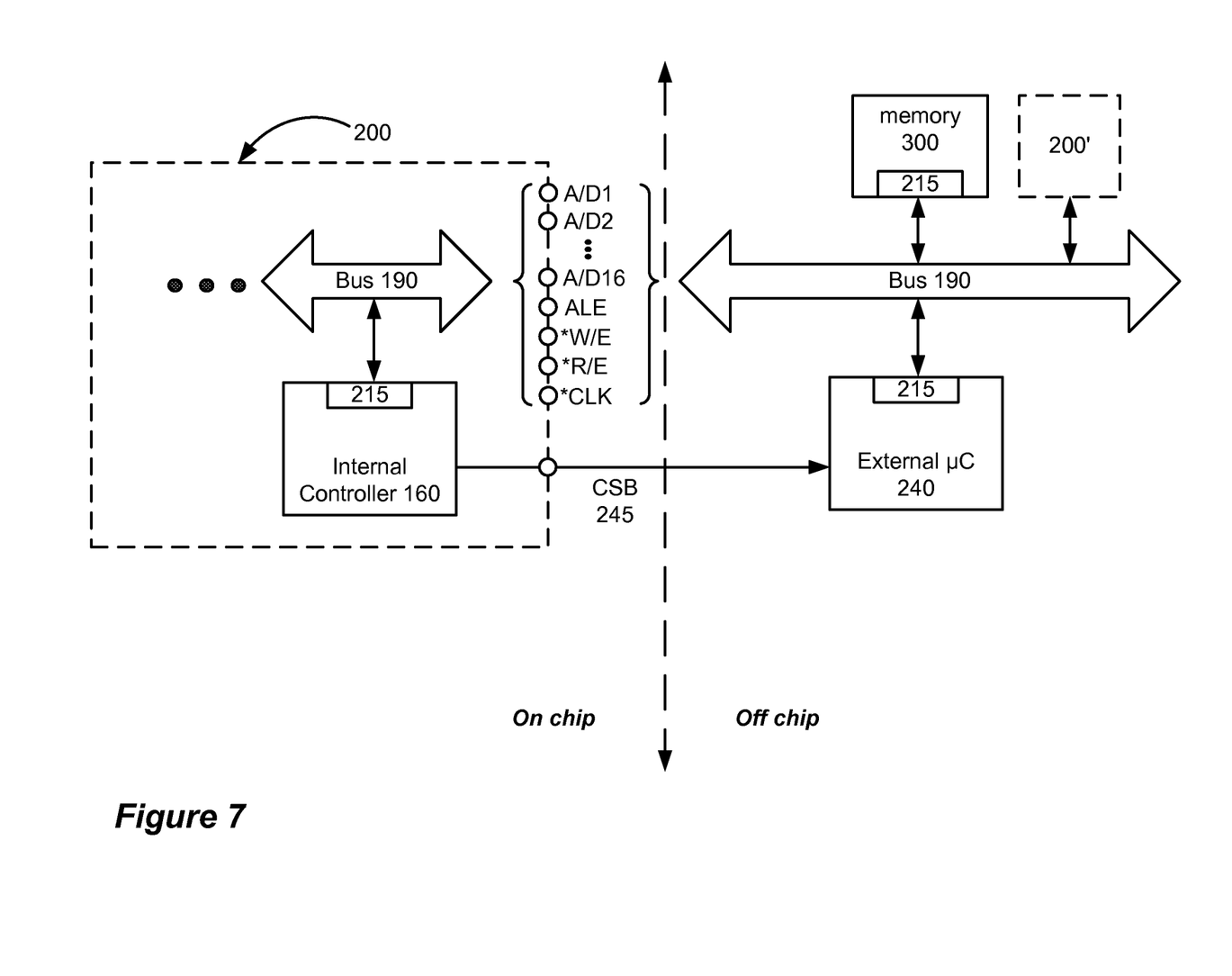
FIG. 7 shows how the improved architecture of FIG. 4 easily provides for additional memory or controller resources outside of an IPG IC built in accordance with the architecture of FIG. 4.

Another advantage of the improved architecture 150 is the ability to easily modify or add functionality to the IPG 100 outside of the IC 200. For example, future improvements may require the IPG to store more data than is otherwise available in the on-chip memory 177 or the off-chip memory 66 (see FIG. 4). In such a case, and if the centralized-bus architecture 150 is used within the IC 200, the bus 190 may be extended outside of the IC 200 as shown in FIG. 7, and more memory 300 (preferably, nonvolatile memory) added. This is of great benefit, because it allows the IPG circuitry to be upgraded without to need to redesign the IC 200 and/or some of its functional blocks.

In another example showing how the disclosed architecture 150 benefits system integration, the capacity of the system can be effectively doubled by the addition of another IC 200' similarly constructed to the first IC 200. This would allow the IPG 100 in which the IC 200 and 200' were placed to provide 32 stimulation electrodes, i.e., 16 each from both of the ICs. In other words, the capacity of the IPG can be increased by simply "daisy chaining" a plurality of stimulation ICs together. In such an embodiment, it may be beneficial that the internal controller 160 in one of the ICs 200 or 200' be inactivated so only one controller 160 acts as the master controller for the system. Alternatively, the IPG system can utilize both controllers 160 in both of the ICs 200 and 200', although this requires arbitration between the two controllers to prevent potential conflicts, a subject discussed below with reference to FIGS. 8-10.

Other devices may also be added external to the IC 200 via the bus 190. For example, one particularly interesting application enabled by the use of architecture 150 is the ability to place at least some degree of systemic control outside of the IC 200. For example, in FIG. 7, an external microcontroller 240 is used to supplant or augment the internal controller 160 resident within the IC 200. (The external microcontroller 240 could comprise the internal controller 160 of an additional IC 200', a point discussed above). Again, the ability to control the IPG via an external controller means that the programming for the IPG can be changed without changes to the IC 200 or the various functional blocks.

Figure 8:
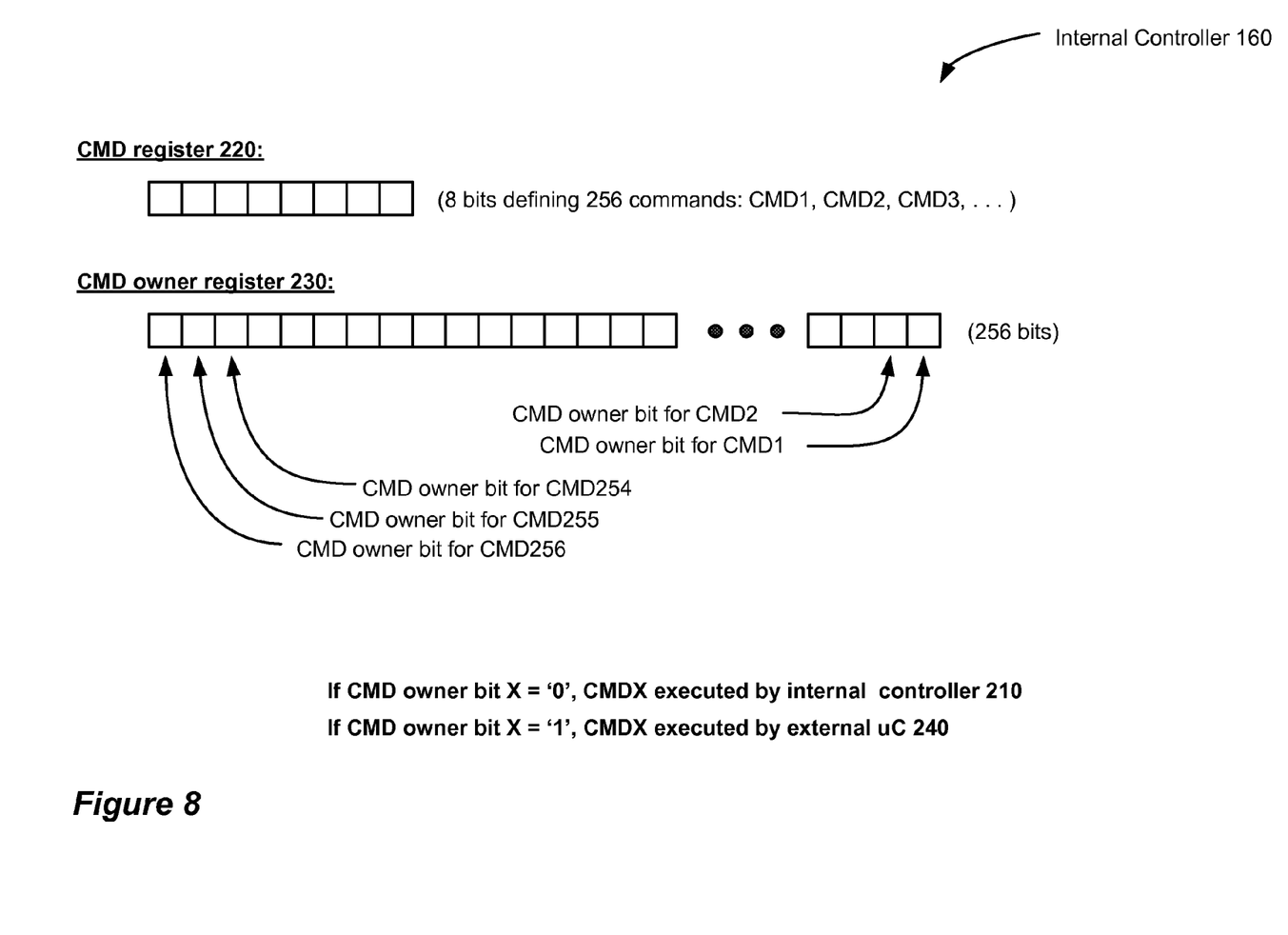
FIG. 8 shows various registers useful in sharing control between an external controller and a controller internal to an IPG IC built in accordance with the architecture of FIG. 4.
Figure 9:
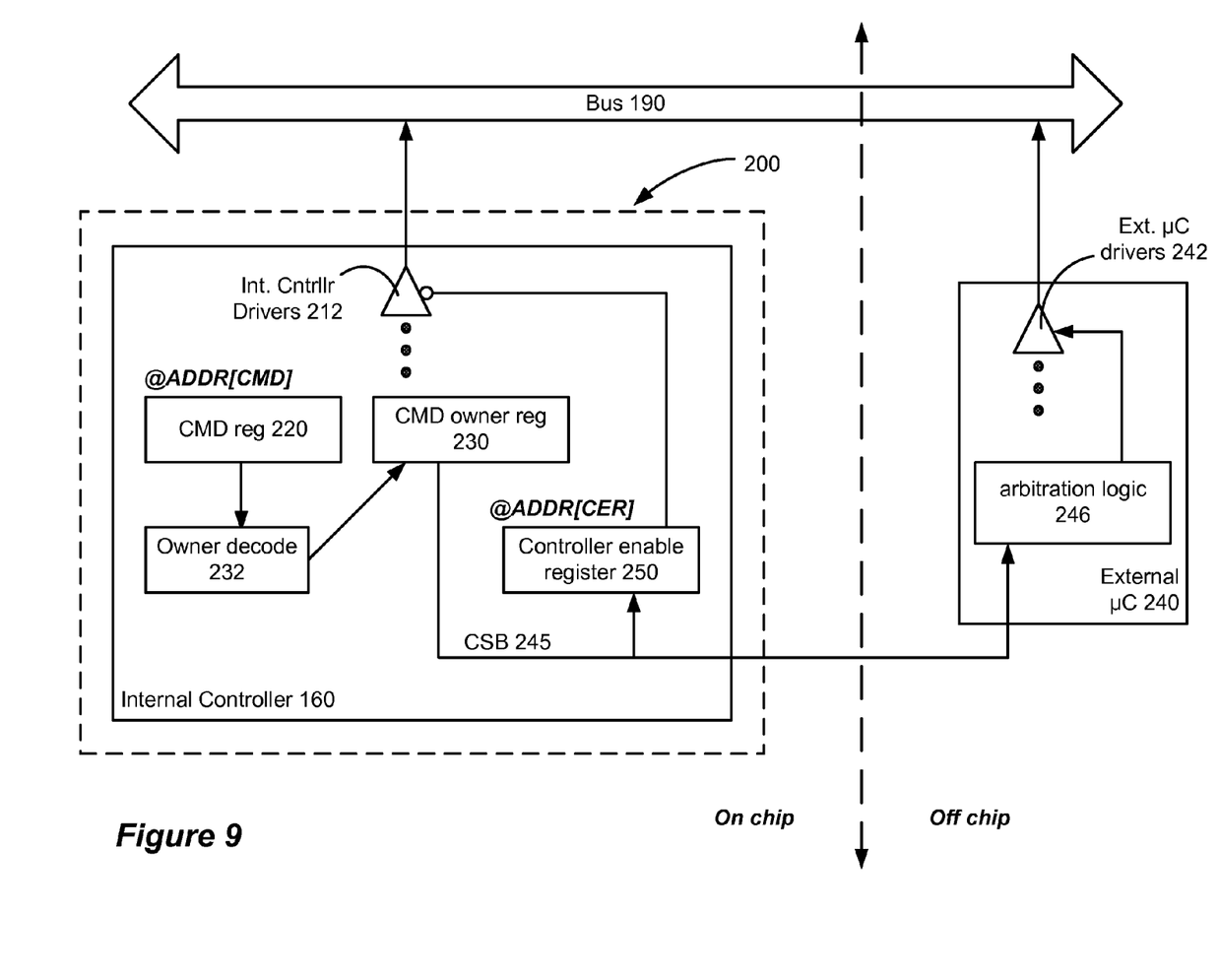
FIG. 9 shows the circuitry useful for sharing control between the external and internal controller of FIG. 8.
Figure 10:
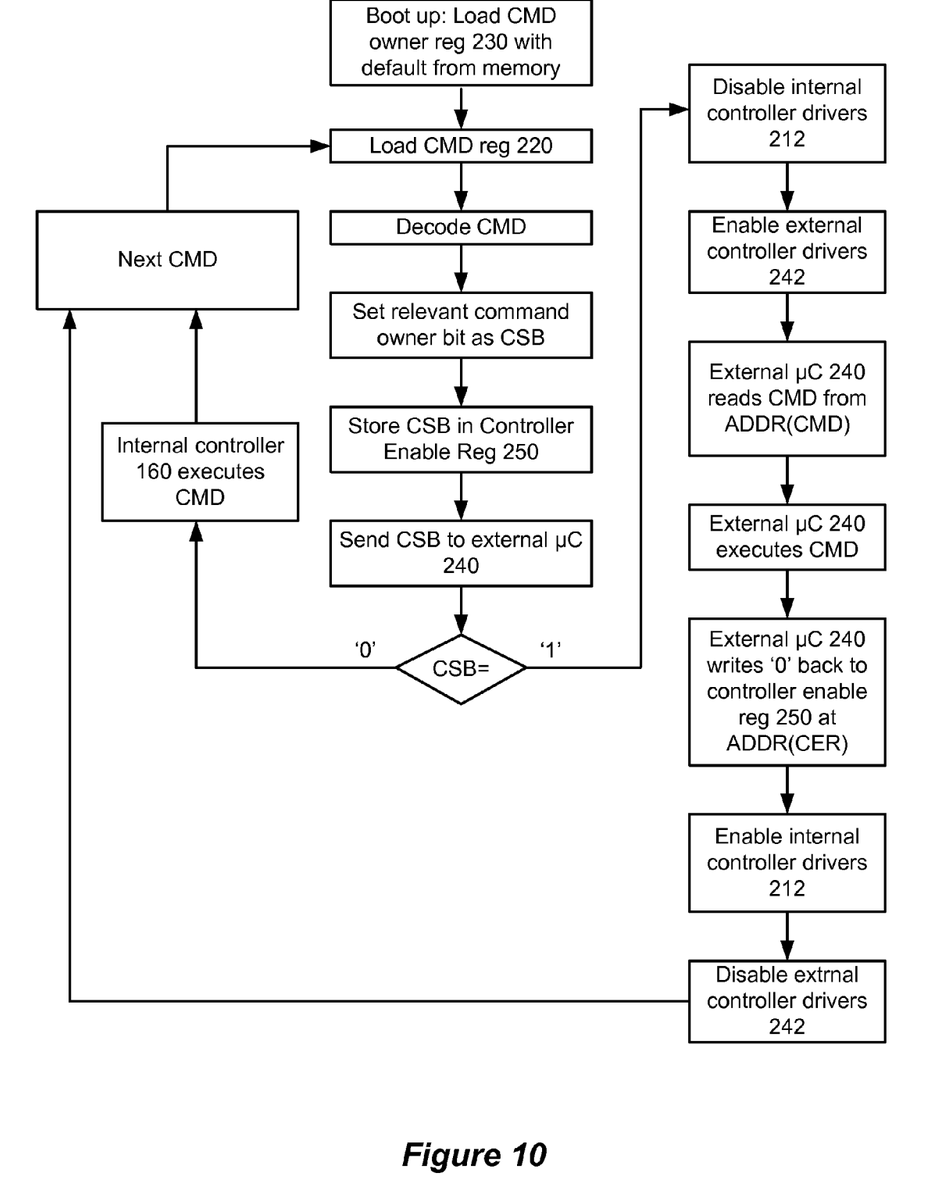
FIG. 10 shows a flow chart discussing the operation of the circuitry of FIG. 9.

However, to add additional control via an external microcontroller 240, additional communications may be required between the internal controller 160 and the external microcontroller 240 to ensure no conflict between the two control mechanisms. FIGS. 8-10 describe how the internal controller 160 and external microcontroller 240 can share control of the IC 200 without conflict.

In recognition of the possibility of external control, the internal controller 160 is provided with additional functionality as illustrated in FIGS. 8 and 9. By way of a quick preview, this additional functionality is designed to recognize whether a particular command issued on the bus 190 is to be handled by the internal controller 160 or the external microcontroller 240. Which device 160 or 240 ultimately processes the command at issue is set by a controller select bit (CSB). If CSB=0, the internal controller 160 executes the command in question; if CSB=1, the external controller 240 executes the command. As can be seen in FIGS. 7 and 9, CSB can comprise a discrete communication signal generally outside of the scope of the centralized bus 190, which due to its discrete nature can be a preferable implementation as a faster and safer method of arbitration between the two controllers 160 and 240.

In other implementations, the controller select bit can comprise data sent via the bus 190 using the bus 190's protocol. In such an implementation, the CSB data could be viewed as a control "token" which is passed between the internal controller 160 and the external microcontroller 240 via the bus 190. Such a purely bus-based method for arbitration between the controllers is easily implemented. However, because it is easier to illustrate the passage of control between the two controllers 160 and 240 using a discrete non-bus based signal approach, that approach is illustrated below and in the figures.

As shown, the internal controller 160 is designed with two registers, a command register 220 and a command owner register 230, shown in detail in FIG. 8. The command register 220 is a standard feature of many controllers, and simply comprises a binary representation of the various commands the IPG can execute. In the example shown, because the command register 220 is eight bits long, the IPG 100 is capable of processing 256 (2^8) different commands. The command owner register 230 is comprised of as many bits as there are relevant commands (in this example, 256), with each bit in the register denoting whether a particular command is to be handled by the internal controller 160 or the external microcontroller 240. As shown, if particular bit in the command owner register 230 is a '0', the corresponding command is to be executed by the internal controller 160; and if a '1,' the external microcontroller 240 will execute the command. In a simple example, if the 256-bit command owner register 230 reads "1010000 . . . 0001," commands 256, 254, and 1 (CMD256, CMD254, and CMD1) would be executed by the external microcontroller 240, with all other commands executed by the internal controller 160.

The use of command register 220 and command owner register 230 to issue a controller select bit (CSB) 245 is illustrated in FIG. 9. Once a command has been received by the command register 220, it is decoded (e.g., demultiplexed) to understand its command number (CMD256 to CMD1). Then, the command number is used to retrieve the appropriate command owner bit from the command owner register 230. This bit is set as the controller select bit (CSB) 245 to indicate which controller (160, 240) is to handle the command as mentioned earlier.

This process is explained in detail with respect to FIG. 10. Upon boot up, the command owner register 230 is loaded with default values from memory (internal memory 177, serial external memory 66, etc.). Normally, the default values of the various command owner bits in the command owner register 230 would be all '0's, denoting that at least initially all commands are to be executed by the internal controller 160. Thereafter, at some point during operation, the command register 220 is loaded with a command at its address (ADDR [CMD]). The command is decoded (demultiplexed) as explained above, and the corresponding command owner bit is issued as the controller select bit (CSB) 245. The CSB 245 is also stored in the controller enable register 250 at its address (ADDR[CER]), which may comprise a single bit, as shown in FIG. 9. The CSB 245 is also sent to the external controller 240.

With the CSB 245 issued, it is now known which of the controllers 160 or 240 is to execute the command in question, and thus various actions are taken accordingly. If CSB='0', denoting the internal controller 160, little needs to be accomplished but for that controller 160 to execute the command. As a default, to ensure that the external microcontroller 240 will not conflict with execution of the command by the internal controller 160, arbitration logic 246 programmed into the external controller 240 disables the external controller's bus drivers 242 upon sensing that CSB=0. In contrast, the internal controller bus drivers 212 are enabled by the stored controller enable register bit 250 (an active low signal). After the internal controller 160 has executed its command, the system waits for the next command, and the method repeats, etc.

However, if CSB='1', denoting the external microcontroller 240, extra steps are taken to allow control to be temporarily shifted to the external microcontroller 240. Specifically, the arbitration logic 246 in the external controller recognizes upon sensing that CSB='1' that it is in control, and enables its bus drivers 242. By contrast, the internal controller bus drivers 212 are disabled. Additionally, upon recognizing that CSB='1', the arbitration logic 246 retrieves the command (i.e., its command) as stored in the command register 220 by requesting a read via the bus 190 from that register's address (ADDR[CMD]). Once received, the external controller 240 executes the command.

With the command executed by the external microcontroller 240, the remaining steps illustrated in FIG. 10 are directed to returning control back to the internal controller 160 prior to the receipt of a next command. After execution of the command, the arbitration logic 246 now writes a '0' in the controller enable register 250, which can be accessed via the bus 190 at its address ADDR[CER]. This in turn once again enables the bus drivers 212 for the internal controller 160. Concurrent with overwriting the controller enable register 250, the arbitration logic 246 disables the bus drivers 242 for the external controller 240. This restores the system to its initial state in which the internal controller 160 assumes control by default, at which point the system awaits its next command, and the method repeats, etc.

The flow of FIG. 10 is just one way to allow the internal and external controllers 160 and 240 to operate together without conflict in accordance with the improved centralized bus architecture 150. However, one skilled in the art will recognize that other flows and circuitry are possible for achieving this same goal, and therefore what is depicted should be understood as merely an example.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable stimulator device, comprising:
   an integrated circuit comprising a plurality of functional blocks, wherein the functional blocks comprise
      one or more first blocks selected from the group consisting of (i) an analog-to-digital converter, (ii) telemetry circuitry configured to communicate with a device external to the implantable stimulator device, and (iii) battery charging circuitry configured to charge a battery in the implantable stimulator device,
      stimulation circuitry configured to provide stimulation pulses to at least one tissue-stimulating electrode coupled to the stimulation circuitry, and
      an interrupt controller configured to receive interrupts issued by one or more of the first blocks and to receive an interrupt issued by the stimulation circuitry; and
   a digital bus directly connected to each of the functional blocks, wherein the functional blocks communicate with each other via a bus protocol, and wherein the interrupts are not communicated on the digital bus.

2. The device of claim 1, wherein one of the functional blocks further comprises a master controller, and wherein all other functional blocks are slaves to the master controller.

3. The device of claim 1, wherein the integrated circuit further comprises an analog bus, wherein the analog-to-digital converter receives a plurality of analog signals on the analog bus from at least some of the functional blocks outside of the digital bus.

4. The device of claim 1, wherein the integrated circuit has external terminals, and wherein the digital bus is directly connected to at least one external terminal to allow the digital bus to communicate with at least one device outside the integrated circuit.

5. The device of claim 4, wherein the device outside the integrated circuit comprises a memory circuit.

6. The device of claim 4, wherein the device outside the integrated circuit comprises a controller.

7. The device of claim 1, wherein the digital bus is a parallel bus.

8. The device of claim 1, further comprising bus interface circuitry interposed between each functional block and the digital bus, wherein the bus interface circuitry allows the functional blocks to communicate with each other via the bus protocol.

9. An implantable stimulator device, comprising:
   a plurality of functional blocks, wherein the functional blocks comprise
      one or more first blocks selected from the group consisting of (i) an analog-to-digital converter, (ii) telemetry circuitry configured to communicate with a device external to the implantable stimulator device, and (iii) battery charging circuitry configured to charge a battery in the implantable stimulator device,
      stimulation circuitry configured to provide stimulation pulses to at least one tissue-stimulating electrode coupled to the stimulation circuitry, and
      an interrupt controller configured to receive interrupts issued by one or more of the first blocks and to receive an interrupt issued by the stimulation circuitry; and
   a digital bus directly connected to each of the functional blocks, wherein communications on the digital bus are governed via a bus protocol, and wherein the interrupts are not communicated on the digital bus.

10. The device of claim 9, wherein one of the functional blocks further comprises a master controller, and wherein all other functional blocks are slaves to the master controller.

11. The device of claim 9, further comprising an analog bus, wherein the analog-to-digital converter receives a plurality of analog signals on the analog bus from at least some of the functional blocks outside of the digital bus.

12. The device of claim 9, wherein the plurality of functional blocks and the digital bus are integrated on a single integrated circuit, and wherein the integrated circuit has external terminals, and wherein the digital bus is directly connected to a plurality of external terminals to allow the digital bus to communicate with at least one device outside the integrated circuit.

13. The device of claim 12, wherein the device outside the integrated circuit comprises a memory circuit.

14. The device of claim 12, wherein the device outside the integrated circuit comprises a controller.

15. The device of claim 9, wherein the digital bus is a parallel bus.

16. The device of claim 9, further comprising bus interface circuitry interposed between each functional block and the digital bus, wherein the bus interface circuitry allows the functional blocks to communicate with each other via the bus protocol.

17. An implantable stimulator device, comprising:
   an integrated circuit comprising a plurality of functional blocks, wherein the functional blocks comprise
      one or more first blocks selected from the group consisting of (i) an analog-to-digital converter, (ii) telemetry circuitry configured to communicate with a device external to the implantable stimulator device, and (iii) battery charging circuitry configured to charge a battery in the implantable stimulator device,
      stimulation circuitry configured to provide stimulation pulses to at least one tissue-stimulating electrode coupled to the stimulation circuitry, and
      an interrupt controller configured to receive interrupts issued by one or more of the first blocks and to receive an interrupt issued by the stimulation circuitry;
   at least one device external to the integrated circuit; and
   a digital bus directly connected to each of the functional blocks and to the external device, wherein the external device and the functional blocks communicate with the digital bus in accordance with a protocol, and wherein the interrupts are not communicated on the digital bus.

18. The device of claim 17, wherein one of the functional blocks comprises a master controller, and wherein all other functional blocks are slaves to the master controller.

19. The device of claim 17, wherein the integrated circuit further comprises an analog bus, wherein the analog-to-digital converter receives a plurality of analog signals on the analog bus from at least some of the functional blocks outside of the digital bus.

20. The device of claim 17, wherein the integrated circuit has external terminals, and wherein each of a plurality of signals that comprise the digital bus is directly connected to an external terminal to allow the digital bus to communicate with the at least one device external to the integrated circuit.

21. An implantable stimulator device, comprising:
an integrated circuit comprising a plurality of functional blocks, each block for performing at least one function within the implantable medical device, at least one block comprising an internal controller for all other functional blocks in the integrated circuit, and wherein at least one of the other functional blocks controlled by the internal controller comprises stimulation circuitry coupled to at least one electrode that delivers electrical stimulation to a tissue of a patient;
an external controller device external to the integrated circuit; and
a digital bus directly connected to each of the functional blocks and to the external controller, wherein the digital bus receives issued commands,
wherein the internal controller comprises controller select circuitry for determining whether an issued command on the digital bus comprises a first command executable by the internal controller or a second command executable by the external controller, and for issuing a controller select signal in accordance with the determination.

22. The device of claim 21, wherein the controller select circuitry comprises a register, each location in the register associated with a particular command, and each location providing the controller select signal for its associated particular command.

23. The device of claim 22, wherein the issued controller select signal is sent to an arbitration circuit in the external controller.

24. A method for operating an implantable stimulator device, comprising:
issuing a command on a digital bus, wherein the digital bus is directly connected to:
an integrated circuit comprising a plurality of functional blocks, wherein one of the functional blocks comprises a first controller, and wherein at least one other functional block comprises stimulation circuitry for the implantable stimulator device, wherein at least one tissue-stimulating electrode is coupled to the stimulation circuitry, and
a second controller, wherein the second controller is external to the integrated circuit;
determining whether the issued command is to be executed by the first controller or the second controller, and issuing a controller select signal in accordance with the determination; and
executing the command at the first or second controller in accordance with the controller select signal.

25. The method of claim 24, wherein the determining step is accomplished by the first controller via decoding the issued command and retrieving the controller select signal from a register in the first controller.

26. The method of claim 25, further comprising having the second controller retrieve the issued command from the first controller when the issued command is to be executed by the second controller.

27. The method of claim 26, further comprising returning control back to the first controller after the issued command is executed by the second controller.

* * * * *